United States Patent [19]

Fernandes et al.

[11] Patent Number: 4,672,056
[45] Date of Patent: Jun. 9, 1987

[54] ERYTHROMYCIN A DERIVATIVES AND METHOD OF USE

[75] Inventors: Prabhavathi Fernandes, Lake Forest; Leslie A. Freiberg, Waukegan, both of Ill.

[73] Assignee: Abbott Laboratories, North Chicago, Ill.

[21] Appl. No.: 797,315

[22] Filed: Nov. 12, 1985

[51] Int. Cl.4 .................. A61K 31/71; C07H 17/08
[52] U.S. Cl. ................................. 514/29; 536/7.2
[58] Field of Search ........................ 536/7.2; 514/29

[56] References Cited

U.S. PATENT DOCUMENTS 4,150,220  4/1979  Sciavolino ................... 536/7.2
4,331,803  5/1982  Watanabe et al. ............ 536/7.2

Primary Examiner—Johnnie R. Brown
Attorney, Agent, or Firm—Martin L. Katz; Michael J. Roth

[57] ABSTRACT

Erythromycin A derivatives with high antimicrobial activity are disclosed. 14-hydroxyerythromycin A and derivatives show superior in vitro antimicrobial activity compared to the parent compounds.

4 Claims, No Drawings

ERYTHROMYCIN A DERIVATIVES AND METHOD OF USE

TECHNICAL FIELD

This invention relates to antibiotics for use in the chemotherapy of antimicrobial infections, and more particularly to an antibiotic based on erythromycin A which exhibits high antimicrobial activity.

BACKGROUND ART

Erythromycin A and common derivatives are widely used and exhibit desirable activity against a number of gram-positive pathogens. Since some pathogens are less susceptible than others to these drugs, high doses of these antibiotics are occasionally necessary in the treatment of serious or widespread infections. In other isntances, combinations of these drugs with other antimicrobials must be employed. As a result, there is a continuing search for antibiotics which are more potent against certain organisms than those currently used. Desirably, such drugs will have an improved therapeutic ratio, which is the ratio of the effective therapeutic or prophylactic dose to the toxic dose, usually expressed in terms of the $ED_{50}/LD_{50}$ ratio.

It is an object of this invention to provide novel compounds which are derivatives of erythromycin, and which have greater in vitro and in vivo potency against certain organisms, such as *Hemophilus influenzae*, than erythromycin A, and preferably greater than the more toxic derivatives of erythromycin A.

This and other objects of this invention will be more fully understood by reference to the following disclosure.

DISCLOSURE OF THE INVENTION

This invention provides novel 14-hydroxyerythromycin A compounds and pharmaceutically acceptable salts and esters thereof. These compounds may be substituted or unsubstituted at the 2'- and/or 4"-positions. The unsubstituted compound has hydroxyl group at the 2'- and 4"-positions like the parent erythromycin compound. In the substituted compounds one or both of the hydroxyl groups are replaced by a pharmaceutically acceptable ester group having from 2 to 20 carbon atoms. In addition, these compounds may be substituted at the 6-position with a methyl or ethyl group. In structural terms, this invention provides compounds of the formula

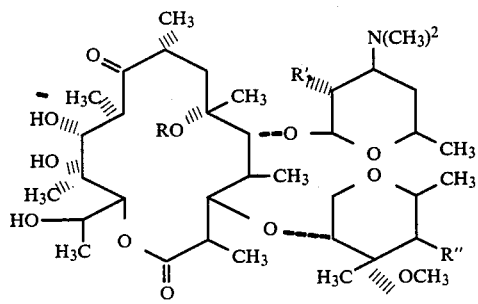

where R is selected from hydrogen, methyl and ethyl, and R' and R" are independently selected from hydroxyl or acyl or 2 to 20 carbon atoms, and pharmaceutically acceptable salts thereof. Especially preferred is 6-O-methyl-14-hydroxyerythromycin A, i.e., a compound according to the foregoing formula in which R is methyl and R' and R" are both hydroxyl.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

The compounds of the present invention can be used in the form of salts derived from inorganic or organic acids. Among the more common salts and esters of macrolide antibiotics are the estolate (lauryl sulfate salt of the propionate ester), ethyl succinate, gluceptate (glucoheptonate), lactobionate, stearate, and hydrochloride forms. Other acid salts used in the pharmaceutical arts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, gluconate, glycero-phosphate, hemisulfate, heptonate, hexanoate, hydro-bromide, hydroiodide, 2-hydroxy-ethanesulfonate, lactate, maleate, methanesulfonate, 2-naphthalenesulfonate, nicotinate, oxalate, pamoate, pantothenate, pectinate, persulfate, 3-phenylpropionate, picrate, pivalate, propionate, succinate, tartrate, thiocyanate, tosylate, and undecanoate. Although quaternized macrolide compounds are, in general, drastically less active than the parent compound in-vivo, basic nitrogen-containing groups can be quaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

This invention also provides methods of treating and preventing infection by susceptible organisms in a human or lower animal host in need of such treatment, which method comprises administration to the human or lower animal host a therapeutically effective amount of a compound or composition of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques.

Total daily dose of the compounds of this invention administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's injection, U.S.P. and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectibles.

Suppositories for rectal administration can be prepared by mixing the drug with a suitable nonirritating excipient such as cocoa butter or a polyethylene glycol which is solid at ordinary temperatures but liquid at the rectal temperature and will therefore melt in the rectum and release the drug.

Solid dosage forms for oral administration may include capsules, tablets, pills, powders, prills and granules. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric and other release-controlling coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well known in the medical arts. In general, treatment regimens according to the present invention comprise administration to a patient in need of such treatment from about 100 milligrams to about 5,000 milligrams (preferably 500 to 2,000 milligrams) of the erythronolide compound of this invention per day in multiple doses or, preferably, in a single dose of from about 250 milligrams to about 1,000 milligrams.

The following examples illustrate the synthesis and use of the compounds and compositions of this invention, without intending to be limitative thereof.

EXAMPLE 1

6-O-methyl-14-hydroxyerythromycin A

This compound was isolated by the following method:

A 4 mL sample of pooled human urine from subjects dosed with 6-O-methylerythromycin A was diluted with 8 mL of 4% sodium bicarbonate solution and the resulting mixture was extracted with 4 mL of benzene. The benzene extract was applied to tlc plates which were developed with a solvent system consisting of a mixture of $CH_3$:$ch_3CN$:MeOH:conc. $NH_4OH$ in the ratio 8.5:1.0:0.5:0.2 respectively. The tlc plates were air dried and zones having an $R_f$ of 0.2 to 0.3 were scraped from the plates and were extracted with methanolic ammonia. The methanol was filtered and evaporated to give 14-hydroxy-6-O-methyl erythomycin A as determined by mass- and proton NMR-spectral data.

M/z: $(M+H)^+ = 764$.

$^1$H-NMR: H 13 4.98 ppm (doublet); 15 $CH_3$ 1.12 PPM (doublet); H 14 4.16 ppm (doublet of quartets).

EXAMPLE 2

Antimicrobial Testing

The susceptibility of 8 different genera and species of bacteria to 6-O-methylerythromycin A and 14-hydroxy-6-O-methyl erythomycin A was measured in vitro using the principles of agar diffusion. Logarithmic phase cultures of bacteria were inoculated on the surface of agar plates. Immediately afterward, micro-wells were cut in the agar and filled with 10 uL of the test compound at a concentration of 100 ug/mL. The plates were incubated at 35° C. for 18 hours and the zones of growth inhibition were measured. The results are shown in the table. 6-O-methylerythromycin A was slightly more active than the 14-hydroxy derivative against *Strep. pneumoniae, Strep. pyogenes, Strep. faecalis, Staph. aureus* and *Bact. fragilis*. However, the 14-hydroxy-6-O-methyl erythomycin A was as active as the parent compound against *E. coli* and *Ps. aeruginosa*, and more active against *H. influenzae*.

The two compounds were tested for combination activity by positioning the microwells approximately 10 mm from each other. No antagonistic activity was seen between the two compounds. The two compounds showed additive or better activity against all organisms.

| Relative Potency of 6-O—methylerythromycin A and 14-hydroxy-6-O—methyl erythomycin A | | |
|---|---|---|
| | Zone Size (mm) | |
| Organism | 6-O—Methyl | 14-OH—6-O—Me |
| S. pneumoniae CMX 635 | 27 | 20.5 |
| S. pyogenes 930 | 10 | 8 |
| S. faecalis 736 F | 17.5 | 15 |
| S. aureus 6538 P | 21 | 18 |
| E. coli Juhl | 5.5 | 5.5 |
| Ps. aeruginosa 5007 | 4.5 | 4.25 |
| H. influenzae CMX 747C | 10 | 12 |
| B. fragilis ATCC 25285 (105) | 24 | 20 |

EXAMPLE 3

Synthesis of 14-hydroxy-6-O-methyl erythromycin A

The title compound is synthesized in an enzymatic fermentation by combining 6-O-methyl erythromycin A with a liver homogenate and incubating the mixture at 37° C. for from 24 to 48 hours. Preferably, a human hepatocyte homogenate from cell cultures or fresh cadaveric sources is used. Alternatively, a liver homogenate from lower animals can be used; however, it has been determined that a rat liver homogenate is relatively inactive in effecting this conversion. Accordingly, other animal sources should be used. The compound can then be isolated from a filtrate of the mixture and purified by the methods used in Example 1

What is claimed is:

1. A compound of the formula

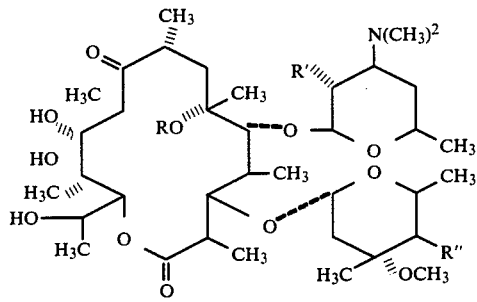

where R is selected from hydrogen, methyl and ethyl, and R' and R" are independently selected from hydroxyl or acyl of 2 to 20 carbon atoms, and pharmaceutically acceptable salts thereof.

2. A compound according to claim 1 wherein R is methyl.

3. A pharmaceutical composition in unit dosage form, comprising a compound according to claim 1 in an amount effective to treat or prevent a bacterial infection, in combination with a pharmaceutical carrier.

4. A method of treating and preventing bacterial infections in humans and lower animals in need of such treatment, comprising administering to the human or lower animal a therapeutically effective amount of the composition of claim 3.

* * * * *